United States Patent [19]

Berzofsky et al.

[11] Patent Number: 5,030,449
[45] Date of Patent: Jul. 9, 1991

[54] SYNTHETIC VACCINE AGAINST AIDS VIRUS

[75] Inventors: Jay A. Berzofsky, Bethesda; Paula M. Hale, Rockville; Anne Hosmalin, Bethesda; Hanah Margalit; John L. Spouge, both of Rockville, all of Md.; James L. Cornette, Ames, Iowa

[73] Assignee: The United States of America as represented by the Secretary of the Department of Health and Human Services, Washington, D.C.

[21] Appl. No.: 222,684

[22] Filed: Jul. 21, 1988

[51] Int. Cl.$^5$ .................. A61K 39/00; A61K 37/02
[52] U.S. Cl. ............................ 424/88; 424/89; 530/326; 530/327; 530/350
[58] Field of Search ............ 424/88, 89; 530/350, 530/326, 327

[56] References Cited

PUBLICATIONS

Palker et al., Proc. Natl. Acad. Sci. U.S.A., vol. 85, pp. 1932–1936, 1988 Mar.
Cease et al., Proc. Natl. Acad. Sci. U.S.A., vol. 84, pp. 4249–4253, Jun. 1987.
Takahashi et al., Proc. Natl. Acad. Sci. U.S.A., pp. 3105–3109, May 1988.
Peter Newmark, Nature, vol. 324, pp. 304–305, Nov. 1986.
Palker et al. "Type Specific Neutralization of HIV With Antibodies to Env-Encoded Synthetic Peptides", Proc. Natl. Acad. Sci, U.S.A., vol. 85, pp. 1932–1936, Mar. 1988.
Takahashi et al., "An Immunodominant Epitope of the HIV Envelope Glycoprotein gp160 recognized by Class I MHC Molecules-Restricted Murine CTL", Proc. Natl. Acad. Sci., vol. 58, pp.3105–3109, May 1988.
Cease et al., "Helper T-cell Antigenic Site Identification in AIDS virus gp 120 Envelope Protein and Induction of Immunity in Mice to the Native Protein Using a 16-Residue Synthetic Peptide," Proc. Natl. Acad. Sci., vol. 84, pp. 4249–423, Jun. 1987.
Clerici et al., 1989, Nature, 339: 383–385.

Primary Examiner—Margaret Moskowitz
Assistant Examiner—Abdel A. Mohamed
Attorney, Agent, or Firm—Birch, Stewart, Kolasch & Birch

[57] ABSTRACT

The invention relates to peptide antigens which stimulate helper T lympocytes which specifically recognize HIV envelope protein, thereby enhancing antibody production and cytotoxic T cells to inhibit expression of an infection caused by HIV virus.

2 Claims, 9 Drawing Sheets

HP-3  EQMHEDIISLWDQSL
HP-4  QMHEDIISLWDQSLK
HP-5  HEDIISLWDQSLK
HP-6  HEDIISLWDQSLK
HP-7  DIISLWDQSLKPCVK
HP-8  WDQSLKPCVKLTPLCV

SYNTHETIC VACCINE AGAINST AIDS VIRUS

TECHNICAL FIELD

The present invention is related generally to the development of a vaccine against human immunodeficiency virus (HIV). More particularly, the present invention is related to providing peptide antigens that stimulate helper T lymphocytes which specifically recognize HIV envelope protein, thereby enhancing antibody production and cytotoxic T cells which inhibit expression of, and infection caused, by HIV virus.

BACKGROUND OF THE INVENTION

The development of a vaccine against the human immunodeficiency virus (HIV) is a crucial step in preventing further spread of acquired immunodeficiency syndrome (AIDS). For safety reasons, a whole virus vaccine may not be practical in the case of HIV. However, any subunit vaccine should contain immunodominant helper T-cell sites that could elicit helper T-cell immunity in response to exposure to the native antigen. Helper T cells are necessary for both B-cell activation by causing B-cell proliferation and differentiation into antibody-producing cells, and for induction of cytotoxic T cells. It should be noted that helper T-cells recognize distinct sites within the protein molecules rather than the entire protein antigen. Among these sites, a few usually elicit the bulk of the response and are, therefore, called "immunodominant." Hence, in order to elicit an effective cytotoxic or immunogenic response, the synthetic antigen should preferably include the immunodominant regions in the molecule. Furthermore, the synthetic antigenic peptide(s) should overcome the problem of MHC restriction often encountered with synthetic, fragment vaccines.

SUMMARY OF THE INVENTION

It is, therefore, an object of the present invention to provide synthetic peptide antigen(s) recognized by T cells of all or most MHC types and which, at least in part, is composed of immunodominant sites which elicit a high degree of helper T-cell response against HIV infection.

It is an additional object of the present invention to provide a synthetic or recombinant fragment vaccine against HIV infection substantially without limitations due to major histocompatibility restriction.

It is another object of the present invention to provide a reagent for determining specificity and/or level of T-cell immunity to the AIDS virus.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 shows amino acid residues of overlapping peptides of the $T_2$(HP5) cluster. The single letter amino acid code is used: A=Ala, C=Cys, D=Asp, E=Glu, F=Phe, G=Gly, H=His, I=Ile, K=Lys, L=Leu, M=Met, N=Asn, P=Pro, Q=Gln, R=Arg, S=Ser, T=Thr, V=Val, W=Trp, Y=Tyr.

FIG. 3 shows the amino acid residues of overlapping peptides in the immunodominant region HP52-57.

DETAILED DESCRIPTION OF THE INVENTION

Figure 1:
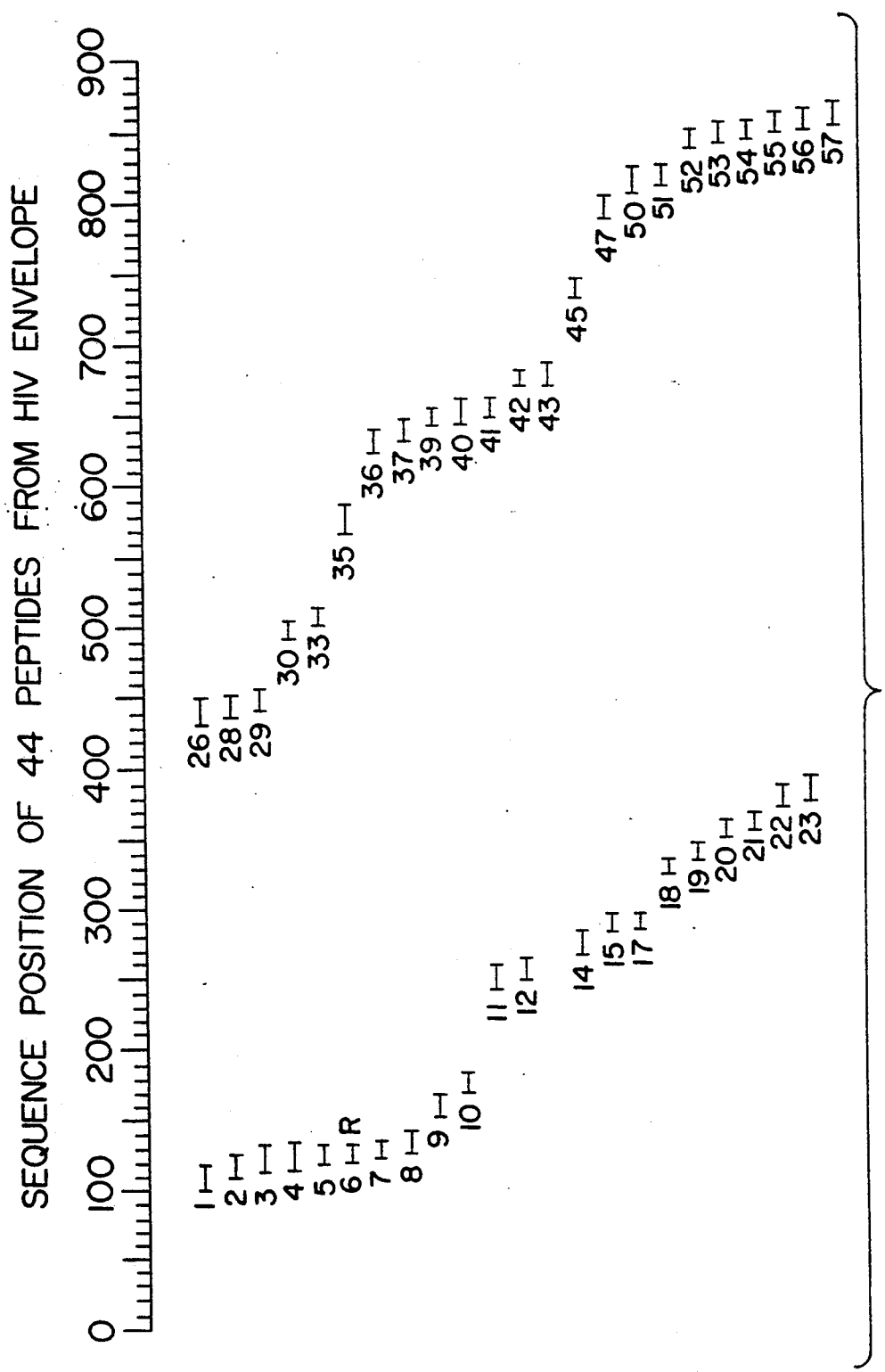
FIG. 1 shows amino acid residues of HIV envelope protein. Amino acid sequence position of the 44 overlapping synthetic peptides is depicted. An arginine is substituted for a carboxy-terminal lysine in HP6 (R). Peptides HP17 and 33 have an extra carboxy-terminal cysteine residue not present in the HIV sequence.

The above and various other objects and advantages of the present invention are achieved by peptide antigens which stimulate proliferation of T-cells capable of recognizing cells expressing HIV envelope protein without restriction across a plurality of diverse MHC types.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "a plurality of MHC class" or types as used herein means at least three or more MHC class or types.

The term "substantially pure" as used herein means as pure as can be obtained by standard purification techniques.

The term "synthetic" peptide as used herein means synthesized by any suitable means such as chemically, by recombinant genetic techniques or the like.

MATERIALS AND METHODS

Mice.

B10.BR/SgSn (H-$2^k$) and B10.D2/nSn (H-$2^d$) mice were obtained from the Jackson Laboratories (Bar Harbor, Me.). B10.S(9R)/Sg (H-$2^{r4}$) and B10.A(5R)/SgSn (H-$2^{i5}$) mice were bred at the NIH breeding colony from breeding pairs obtained from D. J. Stimpfling (Great Falls, Mont.) and from Jackson Laboratories. Mice from the strain B10.S(9R) and B10.A(5R) were chosen because both I-A and I-E molecules of the H-$2^s$ and H-$2^b$ haplotypes are expressed in these recombinant strains, whereas I-E is not expressed in nonrecombinant H-$2^b$ and H-$2^s$ mice.

Antigens.

Recombinant gp160 was prepared from cells infected with a recombinant baculovirus expressing the gene for gp160 of the HTLVIIIB isolate of HIV as described by Rusche et al, 1987, PNAS, USA, 84:6924. It was partially purified by standard lentil lectin chromatography and gel filtration techniques. Synthetic peptides were made by multiple peptide synthesis or the "tea bag" method as described by Houghten et al, 1986, Bio Techniques, 4:522. Peptides were cleaved from their resins by the "low-high" hydrogen fluoride method. Cleaved peptides were desalted by Sep-pak (Waters, Milford, Mass.), and purity and concentration were determined by analytical HPLC. If peptides were insufficiently pure, they were repurified by employing standard preparative HPLC.

Lymph Node T-Cell Proliferation Assay.

Mice were immunized s.c. with 10–30 ug of recombinant gp160 1:1 in complete Freund's adjuvant (CFA) at the base of the tail. (The dose was determined according to the purity of the gp160 preparation.) Eight to ten days later, periaortic and inguinal lymph nodes were removed and prepared in a single-cell suspension in complete T-cell medium in accordance with the method of Berkower et al, 1984, J. Immunol., 132:1370. Lymph node cells at $4 \times 10^5$ cells per well were added to each well of flat-bottomed 96-well microtiter plates (Costar, Cambridge, Mass.). The 44 peptides were added to the wells to make a final volume of 0.2 ml of medium, and each peptide was tested in triplicate. On the fourth day of culture, 1 uCi of [$^3$H]thymidine (6.7 Ci/mmol; New England Nuclear, Boston, Mass.) was added to each well. Eighteen hours later, [$^2$H]thymidine incorporation into DNA, as a measure of proliferation, was determined using liquid scintillation counting. The stimulation index represents a ratio of experimental counts over background counts without antigen.

EXAMPLES

Mice of the H-$2^k$, H-$2^d$, H-$^{i5}$, and H-$2^{r4}$ haplotypes were immunized s.c. in the tail with recombinant gp160 in CFA at a dose of 20–30 ug per mouse. Eight to ten days later the mice were sacrificed, the periaortic and inguinal lymph nodes were isolated, and proliferation of lymph node cells in the presence or absence of antigen was determined as described herein supra.

Figure 3:
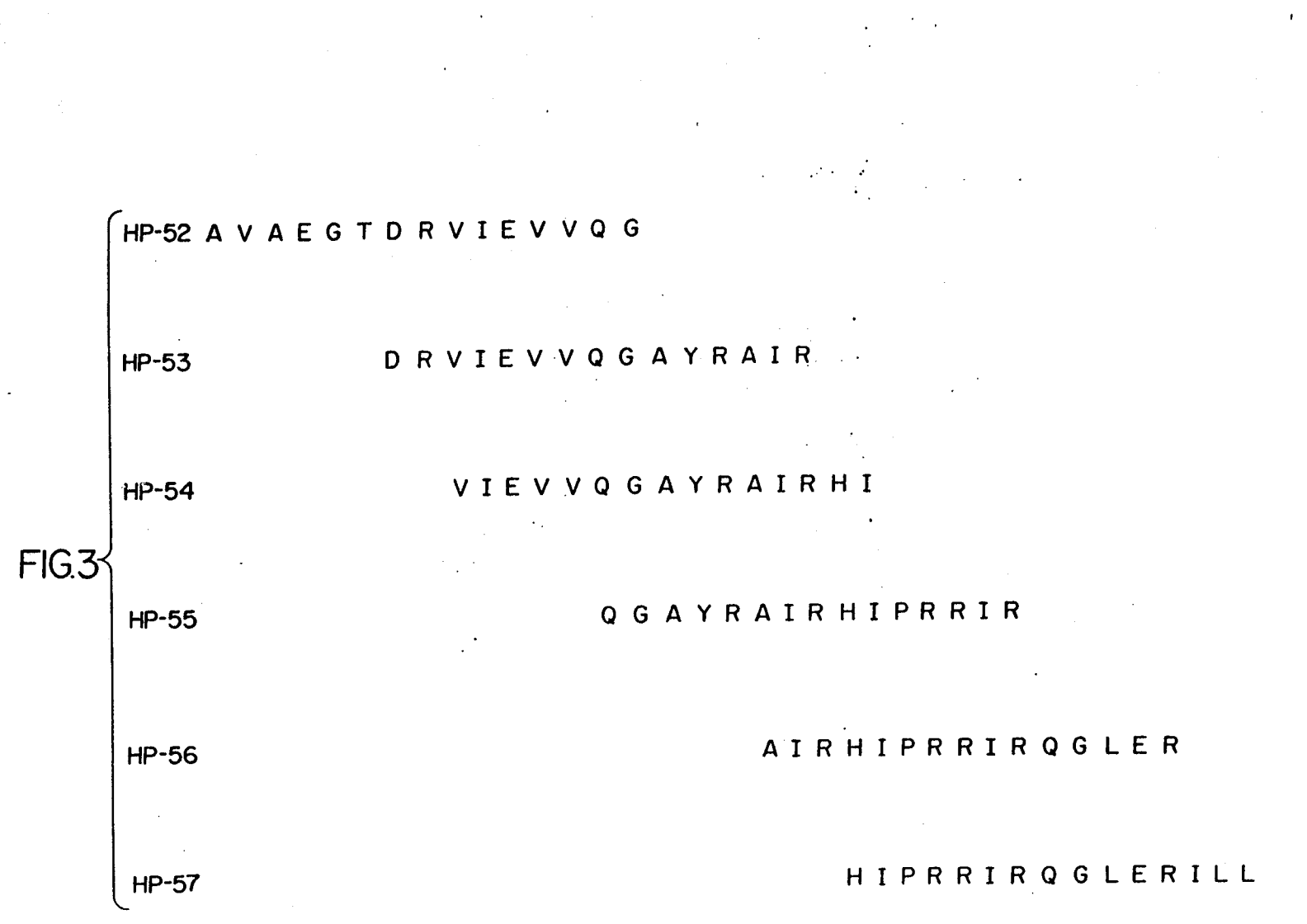

The results of the T-cell proliferation assays in the four haplotypes of mice tested are summarized in Table I. A strong proliferative response was seen in the H-$2^k$ mice to peptides HP4–8 constructed around the previously identified env $T_2$ site (HP5) (FIG. 2). A maximal response was seen with peptides HP5 (residues 112–124, HEDIISLWDQSLK) and HP6 (residues 112–124, HEDIISLWDQSLR), which differ only in the substitution of an arginine for a lysine. A diminishing response was seen to peptides HP4 (residues 110–124, QMHEDIISLWDQSLK), HP7 (residues 114–128, DIISLWDQSLKPCVK), and HP8 (residues 119–134, WDQSLKPCVKLTPLCV). A positive proliferative response was observed to peptide HP26 (residues 428–443, KQIINMWQEVGKAMYA), which is identical to helper T-cell epitope, env $T_2$. This response was seen at a dose of 1 uM. At a dose of 2 uM, the stimulation index was greater than 2 but was not statistically significant. Peptide HP29 (residues 437–451, VGKAMYAPPISGQIR), which overlaps peptide HP26 by six amino acids, also elicited a positive response. In the four haplotypes of mice tested, a positive proliferative response was noted to one or more of the peptides in the cluster of overlapping peptides HP52–57 at the COOH end of the gp41 molecule (FIG. 3). Dose response curves to these peptides in H-$2^k$ mice (FIG. 4) demonstrated a preferential response to peptides HP52 (residues 828–842, AVAEGTDRVIEVVQG) and HP53 (residues 834–848, DRVIEVVQGAYRAIR).

Figure 5:
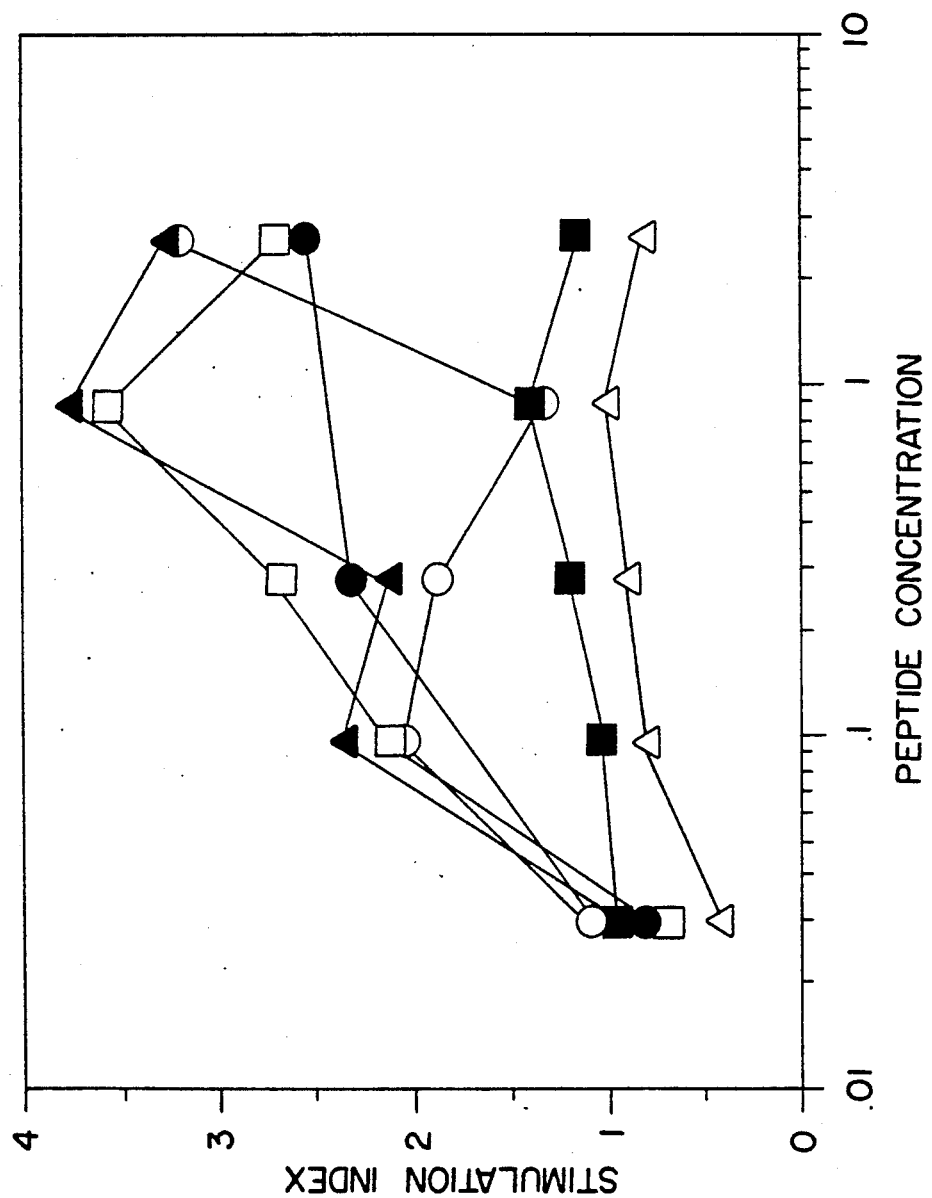
FIG. 5 shows the dose response curves for HP52-57 in B10.D2 (H-$2^d$) mice. B10.D2 mice were immunized with gp160, and triplicate lymph node proliferation assays were performed as described in the text. Response to peptides HP52-57 was assessed with dose response studies. The stimulation index represents the ratio of experimental counts over background counts without antigen.

T-cell proliferative responses to the 44 peptides in mice of the H-$2^d$ haplotype are shown in the second column of Table I. A significant proliferative response to peptide HP3 (residues 109–123, EQMHEDIISLWDQSL) in the env $T_2$ region was observed. Peptide HP3 overlaps HP5 (env $T_2$) but is extended by three amino acids toward the amino terminal end of the molecule and is shorter by one amino acid toward the carboxy terminal end. Positive responses were noted to HP26 (env $T_1$) and to overlapping HP29. In the initial screening, a positive response was seen to HP55 (residues 841–855, QGAYRAIRHIPRRIR) alone in the HP52–57 cluster. Upon closer investigation with dose response studies, positive and preferential responses were seen to peptides HP55 and HP56 (residues 846–860, AIRHIPRRIRQGLER) (FIG. 5). Mice of the H-$2^{r4}$ haplotype (A$^9$E$_\beta^8$E$_\alpha$k) (Table I) did not respond to peptides HP3–8 in the env $T_2$ region. Mice of this strain did respond to the env $T_1$ site peptide HP26, as well as to the overlapping peptides HP28 (432–446, NMWQEVGKAMYAPPI) and HP29. In the initial screening, positive responses were seen to peptides HP55 and HP56 at a dose of 1 uM.

TABLE I

Response of HIV Envelope-Immune Murine T Cells to Synthetic Peptides

| | B10.BR H-2$^k$ S.I. (p<) | B10.D2 H-2$^d$ S.I. (p<) | B10.S(9R) H-2$^{t4}$ S.I. (p<) | B10.A(5R) H-2$^{i5}$ S.I. (p<) |
|---|---|---|---|---|
| HP-1 | 2.3 (.05) | .6 | .7 | 2.23 (.05) |
| HP-2 | 1.18 | .8 | .75 | 1.78 |
| HP-3 | 2.8 | 2.65 (.025) | 1.67 | 2.1 (.0005) |
| HP-4 | 6.52 (.01) | .83 | .98 | 1.53 (.025) |
| HP-5 | 11.2 (.005) | 1.56 | .82 | 1.64 |
| HP-6 | 12.6 (.0025) | 1.02 | 1.26 | 1.78 (.0125) |
| HP-7 | 9.59 (.005) | 1.26 | 1.57 | 1.58 |
| HP-8 | 2.24 (.05) | 1.68 | 1.23 | 1.51 |
| HP-9 | 1.99 (.0005) | 1.75 (.05) | 1.56 | 2.63 |
| HP-10 | 3.55 (.025) | 1.78 | 1.81 | 1.28 |
| HP-11 | 1.8 (.05) | 1.07 | 1.60 (.05) | 1.36 |
| HP-12 | 2.08 | 1.55 | 1.05 | 1.19 |
| HP-14 | 3.24 (.01) | 1.59 | 2.16 | 1.20 |
| HP-15 | 1.89 (.025) | 1.49 | 2.77 (.05) | 1.81 (.0125) |
| HP-17 | 2.28 (.025) | 1.75 | 2.05 | 3.37 |
| HP-18 | 1.98 (.05) | 1.24 | 1.94 (.05) | 1.94 |
| HP-19 | 3.37 (.05) | 3.22 | 1.05 | 1.20 |
| HP-20 | 6.14 (.005) | 1.67 | 3.9 (.01) | 3.31 (.05) |
| HP-21 | 1.65 | 1.21 | .99 | .86$^a$ |
| HP-22 | 2.25 (.05) | 1.99 (.01) | 1.46 | 1.56 |
| HP-23 | 1.48 | 1.14 | 1.63 | 1.07 |
| HP-26 | 2.94 (.025)$^b$ | 3.57 (.0125) | 3.40 (.025) | 1.19 |
| HP-28 | 2.01 | 1.10 | 7.43 (.005) | 1.23 |
| HP-29 | 2.17 (.025) | 2.65 (.05) | 7.05 (.01) | 3.30 (.05) |
| HP-30 | 2.19 (.025) | 2.25 | 5.45 (.01) | .97 |
| HP-33 | 2.41 (.0125) | 2.86 (.05) | 2.6 (.025) | 3.61 (.005) |
| HP-35 | 4.58 (.05) | 1.22 | 5.01 (.01) | 1.0 |
| HP-36 | 1.62 (.025) | 1.02 | 3.83 (.0125) | 2.38 (.05) |
| HP-37 | 4.64 (.005) | 2.11 | 2.35 | 2.17 (.01) |
| HP-39 | 1.93 (.05) | .94 | 3.18 (.025) | 1.66 |
| HP-40 | 3.53 (.0125) | 1.23 | 1.92 | 1.32 |
| HP-41 | 2.34 (.025) | .67 | 1.18 | 1.52 (.05) |
| HP-42 | 1.76 (.05) | 1.81 | 1.69 | 1.58 |
| HP-43 | 1.24 | 1.32 | 1.93 | 2.05 |
| HP-45 | 2.37 (0.05) | 2.10 | 2.08 (.05) | 1.18 |
| HP-47 | 8.58 (.0025) | 2.6 (.05) | 5.26 (.01) | 1.36 |
| HP-50 | 3.04 (.01) | 2.05 (.05) | 2.16 (.05) | 1.73 |
| HP-51 | 2.49 (.025) | 2.15 (.05) | 3.8 (.01) | 1.46 |
| HP-52 | 5.61 (.0125)$^b$ | 1.42 | 1.90 (.05) | 2.49 (.025)$^c$ |
| HP-53 | 10.2 (.005)$^b$ | 1.37 | .67 | 5.39 (.0025)$^b$ |
| HP-54 | 4.04 (.005)$^b$ | 2.3 | .98 | 2.87 (.005)$^b$ |
| HP-55 | 2.99 (.05)$^b$ | 3.0 (.025) | 2.62 (.05)$^b$ | 5.77 (.01)$^b$ |
| HP-56 | 3.43 (.01) | 2.08 | 6.21 (.005) | 2.70 (.025)$^b$ |
| HP-57 | 4.02 (.005) | 1.38 | 1.62 | 2.26 (.05)$^b$ |
| gp160$^d$ | 15.6 (.0025) | 13.9 (.0025) | 8.41 (.005) | 11.4 (.005) |
| gp160$^e$ | | .44 | 7.24 (.005) | |
| PPD$^f$ | 29.7 (.0025) | 16.4 (.0025) | 9.25 (.005) | 12.9 (.025) |

Stimulation indices (S.I.) (experimental cpm/control cpm) with p value (Student's t test experimental versus control) for each peptide in the four strains of mice are shown. Peptides were tested at a concentration of 2 µM unless otherwise noted. Stimulation indices greater than 2 for which the p values are statistically significant are shown in boldface type.
$^a$Peptide concentration of 1.3 µM.
$^b$Peptide concentration of 1 µM.
$^c$Peptide concentration of 0.3 µM.
$^d$gp160 concentration of 0.1 µM.
$^e$gp160 concentration of 0.02 µM.
$^f$PPD concentration of 25 µg/ml.

TABLE II

Number of Strains Strongly Stimulated by Peptides in the Three Categories

| Category of peptide | Number of peptides within the 25% most stimulatory in the following number of strains | | | | | Strong in at least one strain/total |
|---|---|---|---|---|---|---|
| | 0 | 1 | 2 | 3 | 4 | |
| α-helical | 9 | 6 | 9 | 4 | 0 | 19/28 |
| 3$_{10}$-helical | 5 | 1 | 0 | 0 | 0 | 1/6 |
| nonpredicted | 5 | 1 | 1 | 0 | 0 | 2/7 |

The 10 peptides with the strongest response within each strain were identified. Such peptides, for the purposes of this table, are said to stimulate that strain strongly (the 25% most stimulatory peptides). For each of the 41 peptides tested, we determined whether that peptide was among the 25% most stimulatory peptides for none of the strains (0) or for 1, 2, 3, or all 4 of the strains. Shown are the number of peptides in each category strongly stimulating a given number of strains.

Figure 6:
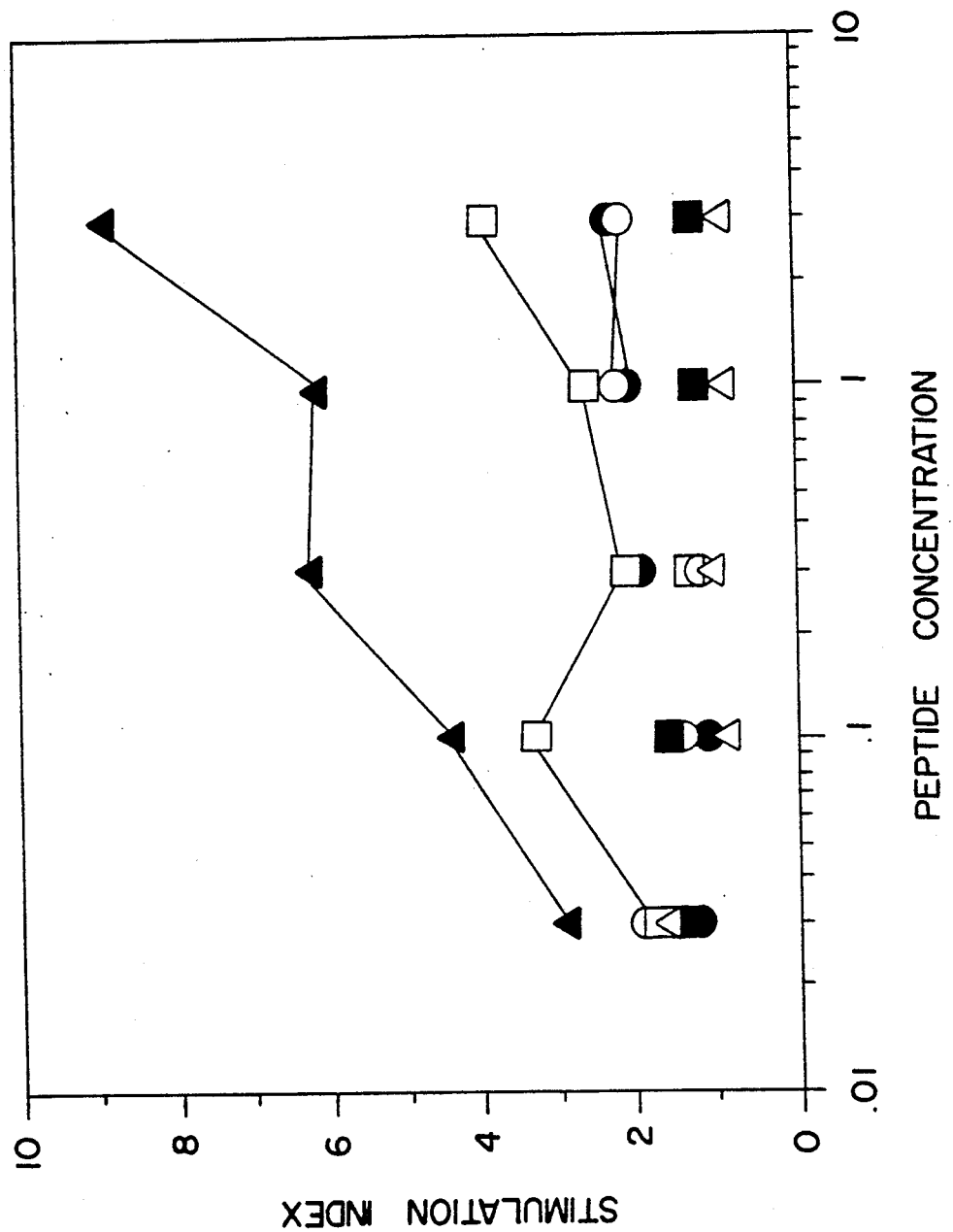
FIG. 6 shows the dose response curves for HP52-57 in B10.S(9R) (H-$2^{t4}$)mice. B10.S(9R) mice were immunized with gp160, and triplicate lymph node proliferation assays were performed as described in the text. Response to peptides HP52-57 was assessed with dose response studies. The stimulation index represents the ratio of experimental counts over background counts without antigen.

The dose response studies confirmed these findings, with preferential responses to HP55 and HP56 (FIG. 6).

Figure 7:
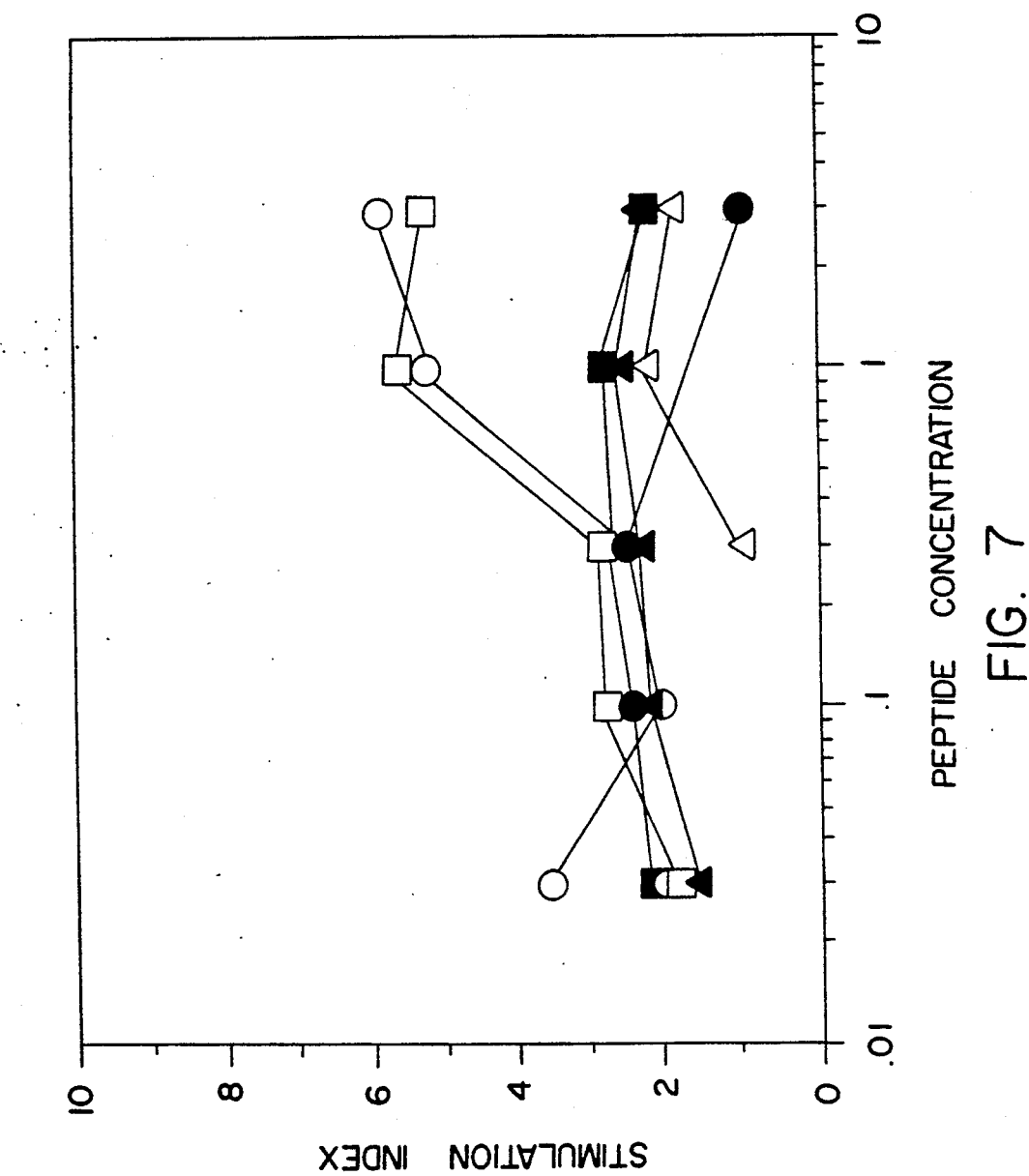
FIG. 7 shows the dose response curves for HP52-57 in B10.A(5R) (H-$2^{i5}$) mice. B10.A(5R) mice were immunized with gp160, and triplicate lymph node proliferation assays were performed as described in the text. Response to peptides HP52-57 was assessed with dose response studies. The stimulation index represents the ratio of experimental counts over background counts without antigen.
Figure 8:
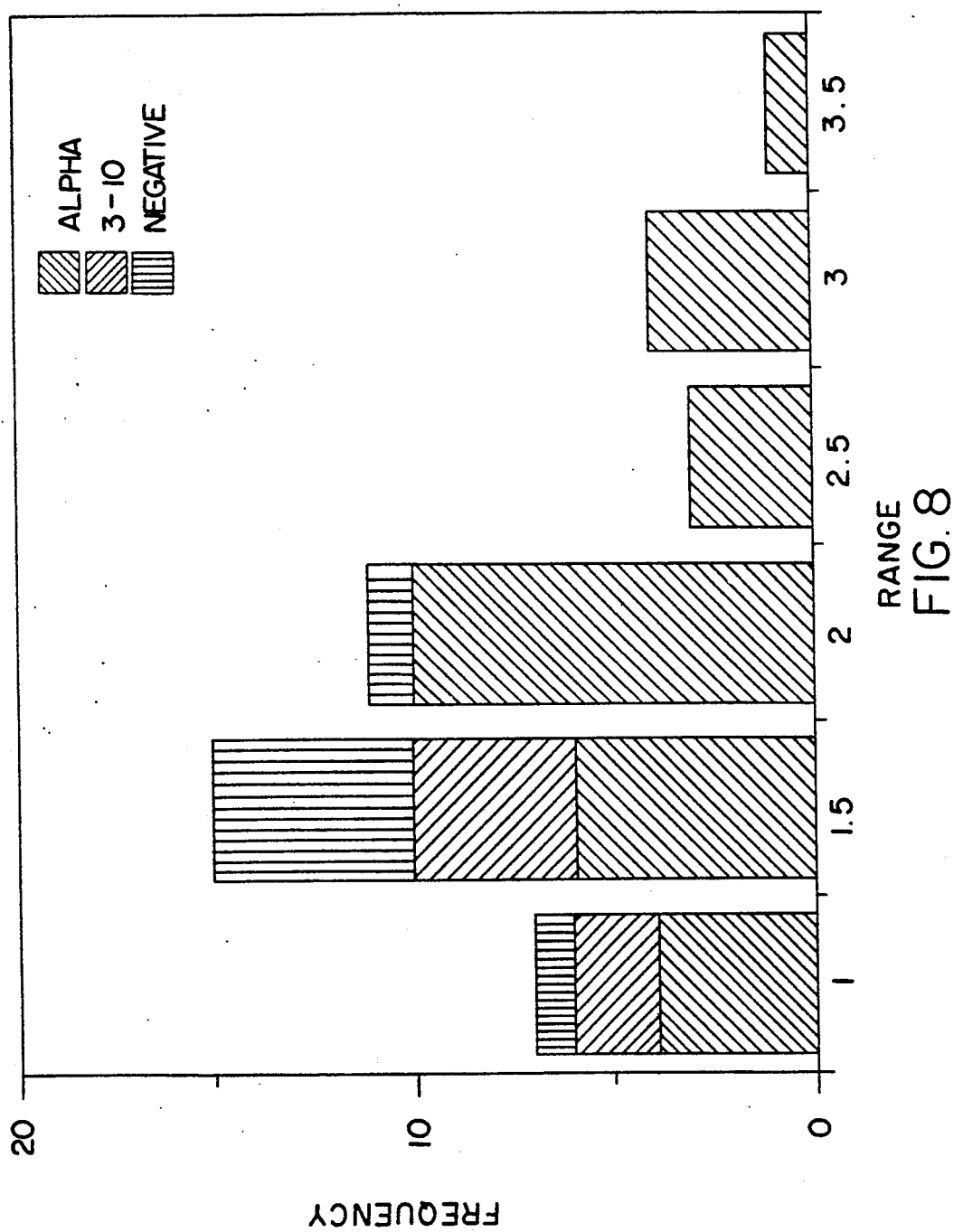
FIG. 8 represents a histogram showing the number of peptides with a geometric mean response lying within the indicated ranges. The lower limit of these ranges is indicated on the X-axis (for example, "1.5" indicates a range of 1.5 to 2.0).

Mice of the H-2$^{i5}$ (A$^b$E$_\beta^b$E$_\alpha^k$) haplotype responded to peptide HP3 in the env T$_2$ region rather than HP5 as did mice of the H-2$^d$ haplotype. On initial screening, all of the peptides in the HP52–57 cluster elicited positive responses. However, on further investigation with dose response studies (FIG. 7), maximal responses were seen to peptides HP53 and HP55.

Peptides from regions other than the T$_1$ or T$_2$ sites and the HP52–57 cluster were found to be positive in some of the strains tested. Positive responses were seen to peptides HP30 (residues 483–497, RDNWRSELYKYKVVK), HP35 (residues 560–581, NNLLRAIEAQQHLLQLTVWGIK), HP47 (residues 787–801, RIVELLGRRGWEALK), HP50 (residues 801–815, KYWWNLLQYWSQELK), and HP51 (residues 806–820, LLQYWSQELKNSAVS) in three of the four strains tested. Peptides HP29 and HP33 elicited positive responses in all of the strains. Several of these immunogenic peptides overlap. Peptides HP30 and HP33 overlap by five residues. Mice of the H-2$^{i5}$ haplotype did not respond to HP30 but did respond to peptide HP33, which extends nine residues toward the carboxy terminal end of the molecule. Similarly, a response to peptide HP26 (env T$_1$ site) was not seen in H-2$^{i5}$ mice, but a response was seen to the overlapping peptide HP29, which extends eight residues toward the carboxy terminal end of the molecule. The most striking responses to overlapping peptides in all of the strains were those seen to peptides in the cluster HP52–57.

These results reflecting T-cell proliferative responses to overlapping peptides of the gp160 envelope protein in four MHC haplotypes of mice immunized with the gp160 molecule confirm that env T$_1$ and T$_2$ sites represent immunogenic regions. Mice of the H-2$^k$, H-2$^d$, and H-2$^{r4}$ haplotypes responded to the env T$_1$ site. H-2$^{i5}$ mice responded to the overlapping peptide HP29. The env T$_2$ site, peptide HP5, was recognized by mice of the H-2$^k$ haplotype, while H-2$^d$ and H-2$^{i5}$ mice recognized the overlapping peptide HP3.

Thus, five peptides (HP30, 35, 47, 50, and 51) have been identified which are recognized as T-cell epitopes by three of the four strains tested and two peptides (HP29 and 33) recognized by all of the strains tested. Peptides 47, 50, and 51 form a cluster of overlapping epitopes. In addition, a cluster of peptides (HP52–57) has been identified as a helper T-cell epitope in the COOH region of the gp41 molecule, to which each strain of mice responded. This characteristic is particularly significant in the preparation of a vaccine, since it is found in the gp41 molecule, a relatively conserved region compared with the many highly variable regions of the gp120 molecule. Mice of the four haplotypes tested responded to different peptides within this cluster.

Figure 4:
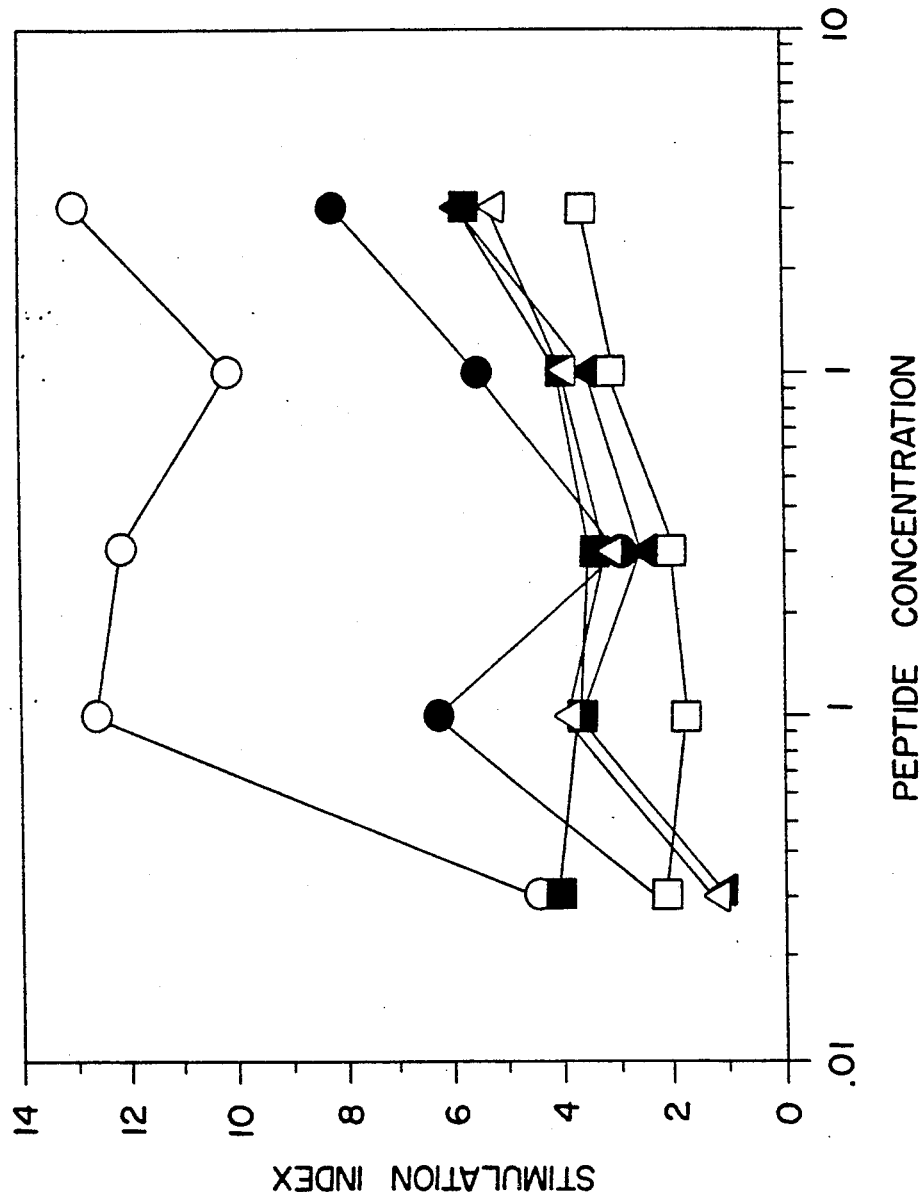
FIG. 4 shows the dose response curves for HP52-57 in B10.BR (H-$2^k$) mice. B10.BR mice were immunized with gp160, and triplicate lymph node proliferation assays were performed as described in the text. Response to peptides HP52-57 was assessed with dose response studies. The stimulation index represents the ratio of experimental counts over background counts without antigen.

Mice of the H-2$^d$ haplotype responded preferentially to peptides HP55 and HP56. This result suggests that the T-cell epitope of consequence may be amino acid sequence AIRHIPRRI, representing the overlapping amino acids of HP55 and HP56 (FIG. 4). Alternatively, two distinct sites may be present in the two overlapping peptides. Mice of the H-2$^{r4}$ haplotype showed a similar response; again, peptides HP55 and HP56 were preferentially recognized. Thus, the recognition site for T cells of the H-2$^{r4}$ haplotype may map to the same nine amino acid sequence. In contrast, mice of the H-2$^k$ haplotype demonstrated a proliferative response primarily to peptides HP52 and HP53, thus mapping the site to the nine amino acids shared by the two peptides (DRVIEVVQG). Mice of the H-2$^{i5}$ haplotype responded maximally to peptides HP53 and HP55. The overlap of these peptides suggests that the T-cell epitope is an eight amino acid sequence QGAYRAIR, although again, the two peptides might alternatively represent two distinct sites.

The discovery of four overlapping epitope clusters (peptides 3–8, 26–29, 47–51, and 52–56) constituting immunodominant sites with respect to the AIDS virus has important implications for the development of a vaccine against the AIDS virus. While a single peptide is not immunogenic in all strains of mice tested, extending the peptide sequence by several amino acids, as in the case of HP5, 26, and 30, elicited a response from mice of more haplotypes. Thus, such extended peptides are more relevant for an outbred population such as humans. The discovery of the cluster of peptides HP52–57 located in a relatively conserved region of the AIDS envelope has particular significance for a vaccine for human trials. Although this cluster of peptides is on the intracellular portion of gp41, T-cell recognition would not be impaired because, unlike antibodies, T cells do not require that the native protein be on the surface of the presenting or target cell; they can recognize processed fragments in association with MHC molecules.

Clearly, an important feature of the present invention is the discovery of epitope clusters recognized by most MHC haplotypes and the observation that extending peptide epitopes by a few residues produces a single peptide recognized by individuals of all haplotypes tested. This discovery for the first time provides a means to overcome the serious problems of MHC restriction and Ir genes in peptide or fragment vaccines aimed at eliciting T-cell immunity, particularly with respect to HIV infection.

Figure 9A:
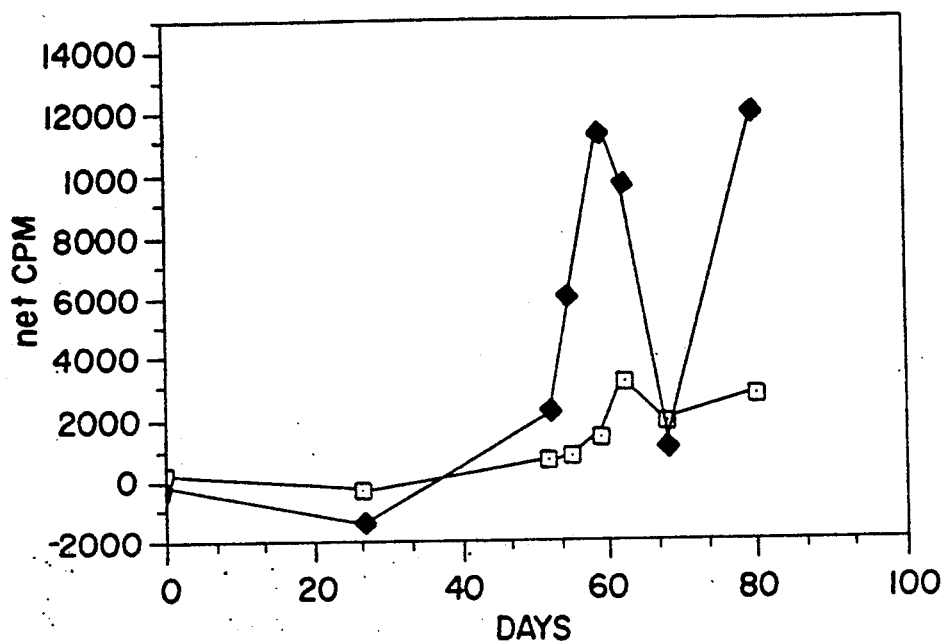
FIG. 9 shows the result when Rhesus monkeys were primed on days 0 and 39 with (1) group 1: 39 nanomoles of each of the three peptides HP5, HP26 and HP53, in emulsion with complete Freund's adjuvant (CFA); (2) GROUP 2: CFA. The monkeys were immunized on day 47 with 0.2 nanomoles gp160 in incomplete Freund's adjuvant (IFA). Anti-gp41 antibodies were measured on days 0, 27, 52, 55, 59, 62, 68 and 80. The results are expressed as 'net cpms': 125-I-protein A bound to the antibodies on the gp41 band of a Western blot, minus the background (prebleed sera: 642±187 cpm).
Figure 9B:
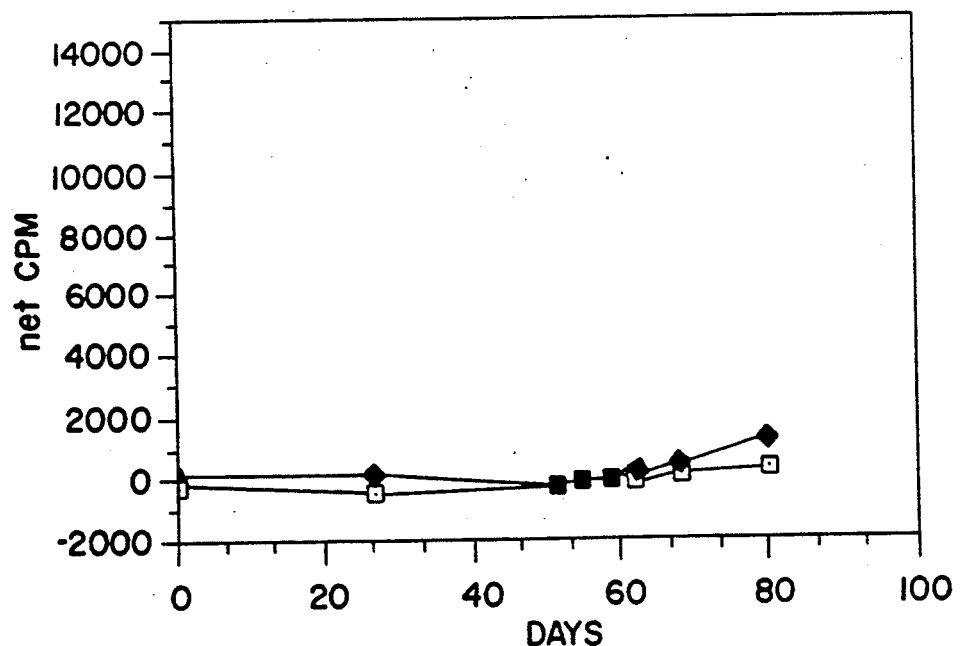

To assess whether these peptides were immunogenic also in primates, and whether they were capable of priming helper T cells to help for a secondary antibody response to the native HIV envelope protein in vivo, Rhesus monkeys were immunized with representatives of three of the clusters, namely peptides HP5, HP26, and HP53. As shown in FIG. 9, the two monkeys of group 1, which were immunized with a mixture of these three peptides before immunization with the native envelope protein gp 160, produced a much enhanced antibody response to the envelope protein (gp41 portion) compared to group 2 monkeys, which did not receive peptide before the whole gp 160. Therefore, these peptides can be used to immunize primates to prime helper T cells to induce a greatly enhanced antibody response to the HIV viral envelope. Furthermore, the monkeys of group 1 showed a good peripheral blood mononuclear cell proliferative response to both HP26 and HP53. The results indicate that these peptides can induce T-cell help in vivo as well as proliferation, and that they can be used to immunize primates as well as mice.

It may be pertinent to note here that live virus vaccines and killed whole or subunit virus vaccines for AIDS have potential safety risks. In contrast, synthetic peptides such as described herein, are inherently safe. Furthermore, molecules corresponding to whole viral proteins but made by recombinant DNA technology contain, in addition to protective epitopes, structures which potentially elicit suppression of the immune response, and structures which elicit antibodies that, rather than being protective, may enhance viral uptake and thus be deleterious. Hence, a vaccine which contains only selected peptides that elicit the appropriate type of immunity and do not have other deleterious effects should, of course, be more desirable for a difficult virus such as HIV. The present invention provides such a vaccine.

Our study by Cease et al, 1987, Proc. Natl. Acad. Sci. 84:4249–4253 defines two synthetic peptides that stimulate helper T-cell immunity to the AIDS virus. However, these peptides are not seen by individuals of all major histocompatibility types. To cover the entire population, one will need additional peptides. The present invention for the first time provides such additional peptides, including ones that are recognized by T-cells from all MHC types of mice tested as well as several monkeys tested.

As to the diagnostic or prognostic use, antibodies are currently the only immune response which is measured. However, there is an interval ranging from weeks to months after infection in which the infected individual may not make antibodies and therefore would test as negative. During this time, such an individual could infect others or donate infected blood. Helper T-cells are believed to appear earlier in the immune response than antibodies, and therefore a test to detect helper T-cells is able to detect infection earlier than the currently used antibody-based tests. Only limited purified protein can be made from the virus, and recombinant molecules are usually contaminated with other material from the vector that could give false positive results. In addition, many of these materials have proven to be mitogenic and therefore would give false positives. In contrast, synthetic peptides such as those described herein are highly purified and not mitogenic. Moreover, by using different peptides described herein, one could detect different sets of T-cells that may vary in the course of the disease and which would not be distinguished using whole protein antigens. Therefore, the synthetic peptides of the present invention are quite useful for determining disease course and to aid in prognosis. This is easily accomplished by performing standard immunological testing such as peripheral blood proliferative blast transformation assays and the like well known to one of ordinary skill in the art.

In summary, the invention provides a set of synthetic peptides which have been shown to be the major sites of recognition within the AIDS viral envelope protein by helper T-cells in four diverse Major Histocompatibility types. The peptides correspond to residues 828–860 (and overlapping peptides therein), 109–124, 432–446, 437–451, 483–497, 492–506, 560–581, 787–801, and 806–820 of the AIDS viral envelope sequence (BH10 isolate) described by Ratner et al., *Nature* 313:277, 1985, with specific amino acid residue sequences described herein above. The invention includes all recombinant or natural peptides selected due to their inclusion of these sites and all synthetic peptides overlapping these sequences or comprising variants of these sequences, for instance corresponding to the same sites on other variant isolates of the AIDS virus; their use for immunization in any vehicle, adjuvant, route of administration, or in combination with other material to elicit T-cell immunity; and their use as diagnostic or prognostic reagents for assessing the quality or quantity of T-cell immunity to the AIDS virus. Of course, the peptides can be used either singly or as a combination of more than one peptides of the present invention. A method for inducing immune response comprises administering to a host susceptible to infection by HIV envelope protein, effective amount of the antigen of the present invention to induce proliferation of helper T-cells immune to HIV infection. A test for determining exposure to the HIV envelope protein comprises incubating peripheral blood mononuclear cells from a blood sample with the peptides of the present invention, and determining the occurrence of proliferation, blast transformation or lymphokine production by conventional immunological techniques, such as those described above, a positive reaction being indicative of said individual having been exposed to HIV envelope protein.

A kit for diagnostic or prognostic test for AIDS, in accordance with the present invention, comprises containers containing the antigenic peptides of the present invention either alone or in combination, and instructional material for performing the test.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A synthetic peptide antigen free from other HIV envelope protein which is a member selected from the group consisting of HP 3–4, HP 7–8, HP 28–30, HP 33, HP 35 and HP 47–56.

2. The antigen of claim 1, which is HP 53.

* * * * *